(12) United States Patent
Yada et al.

(10) Patent No.: US 7,148,373 B2
(45) Date of Patent: Dec. 12, 2006

(54) PROCESS FOR PURIFYING (METH)ACRYLIC ACID AND PROCESS FOR PRODUCING (METH)ACRYLIC ESTERS

(75) Inventors: Shuhei Yada, Yokkaichi (JP); Kenji Takasaki, Yokkaichi (JP); Yasushi Ogawa, Yokkaichi (JP); Yoshiro Suzuki, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 159 days.

(21) Appl. No.: 11/006,806

(22) Filed: Dec. 8, 2004

(65) Prior Publication Data

US 2005/0171382 A1  Aug. 4, 2005

Related U.S. Application Data

(63) Continuation of application No. PCT/JP04/14593, filed on Oct. 4, 2004.

(30) Foreign Application Priority Data

Dec. 24, 2003  (JP)  ............................. 2003-426912

(51) Int. Cl.
*C07C 69/52* (2006.01)

(52) U.S. Cl. ...................... 560/205; 562/600

(58) Field of Classification Search .................... None
See application file for complete search history.

(56) References Cited

U.S. PATENT DOCUMENTS 4,269,705 A * 5/1981 Yoshioka et al. ........... 562/600

FOREIGN PATENT DOCUMENTS

| JP | 09-157213 | 6/1997 |
| JP | 10-237012 | 9/1998 |
| JP | 10-306052 | 11/1998 |
| JP | 2001-213839 | 8/2001 |

* cited by examiner

*Primary Examiner*—Paul A. Zucker
(74) *Attorney, Agent, or Firm*—Nixon & Vanderhye P.C.

(57) ABSTRACT

There is provided a process for purifying (meth)acrylic acid by efficiently removing transition metal components from crude (meth)acrylic acid containing the transition metal components as impurities. When the crude (meth)acrylic acid containing the transition metal components as impurities is contacted with the cation exchange resin to remove the transition metal components therefrom, water is previously added to the crude (meth)acrylic acid prior to contacting the crude (meth)acrylic acid with the cation exchange resin. In the preferred embodiment of the present invention, the transition metal component is manganese.

4 Claims, No Drawings

PROCESS FOR PURIFYING (METH)ACRYLIC ACID AND PROCESS FOR PRODUCING (METH)ACRYLIC ESTERS

This is a continuation application of International Application PCT/JP2004/14593 filed Oct. 4, 2004. The entire content of this application is incorporated herin by reference.

TECHNICAL FIELD

The present invention relates to a process for purifying (meth)acrylic acid and a process for producing (meth)acrylic esters.

BACKGROUND ARTS (Meth)acrylic esters have been used in various applications as raw materials of paints, adhesives, tackifiers, synthetic resins, fibers or the like. The (meth)acrylic esters have been generally produced by the method of subjecting (meth) acrylic acid and alcohol to esterification reaction in the presence of an acid catalyst.

The (meth)acrylic acid used in the esterification reaction have been usually produced by subjecting propylene to gas-phase oxidation reaction and dehydration reaction, and then purifying the resultant product to remove low-boiling impurities and high-boiling impurities therefrom. There have been proposed industrially advantageous methods in which acrylic acid is purified at low costs by omitting the step of removing high-boiling impurities (for example, Japanese Patent Application Laid-open (KOKAI) Nos. 9-157213, 10-237012, 10-306052 and 2001-213839).

However, in the case where the acrylic acid still containing high-boiling impurities which is obtained by the above methods is subjected to esterification reaction, the following problems are caused. That is, the acrylic acid contains, in addition to the high-boiling impurities, transition metal components derived from a polymerization inhibitor used in the step of purifying the acrylic acid. When the acrylic acid containing such transition metal components is subjected to the esterification reaction, an esterification reaction catalyst used therein tends to be significantly influenced by the transition metal components. For example, in the case where the esterification reaction catalyst is in the form of a solid acid catalyst, the transition metal components tend to be absorbed on active sites of the catalyst, resulting in deactivation of the catalyst. Further, in the case of organic acid catalysts, the transition metal components are reacted with the organic acid to form a complex therewith and, therefore, then insolubilized and precipitated, resulting in occurrence of clogging in conduits as well as failure to continue a stable operation for long period of time.

On the other hand, even when the above acrylic acid containing the high-boiling impurities is purified using high-boiling impurity separation column, the purified acrylic acid distilled off from a top of the high-boiling impurity separation column tends to contain the transition metal components owing to entrainment of splash upon the distillation. Therefore, even though such a purified acrylic acid is subjected to the esterification reaction, the esterification reaction catalyst also tends to suffer from the same significant problems as described above.

DISCLOSURE OF THE INVENTION

PROBLEM TO BE SOLVED BY THE INVENTION

The present invention has been made for solving the above problems. An object of the present invention is to provide a process for purifying (meth)acrylic acid by efficiently removing transition metal components from crude (meth)acrylic acid containing the transition metal components as impurities, as well as an improved process for producing (meth)acrylic esters which can be prevented from undergoing deactivation of an acid catalyst used in the esterification reaction, can solve the above problems such as clogging in apparatuses, and can ensure stable production of the (meth)acrylic esters for a long period of time, by using the purified (meth)acrylic acid obtained by the above process as the raw material.

MEANS FOR SOLVING THE PROBLEM

As a result of the present inventors' earnest studies for solving the above problems, it has been found that when the crude (meth)acrylic acid containing transition metal components as impurities is contacted with a cation exchange resin to remove the transition metal components therefrom, removal of the transition metal components can be conducted in an extremely efficient manner by previously adding water to the crude (meth)acrylic acid. The present invention has been attained on the basis of the above finding.

To accomplish the aim, in a first aspect of the present invention, there is provided a process for purifying (meth) acrylic acid by contacting crude (meth)acrylic acid containing transition metal components as impurities with a cation exchange resin to remove the transition metal component therefrom, water being previously added to the crude (meth)acrylic acid prior to contacting the crude (meth)acrylic acid with the cation exchange resin.

In a second aspect of the present invention, there is provided a process for producing a (meth)acrylic ester by reacting (meth)acrylic acid with alcohol in the presence of an acid catalyst, the (meth)acrylic acid obtained by the above purification process being used as the raw material.

EFFECT OF THE INVENTION

Thus, according to the present invention, there is provided a process for purifying (meth)acrylic acid by efficiently removing transition metal components from crude (meth) acrylic acid containing the transition metal components as impurities, as well as an improved process for producing (meth)acrylic esters which can be prevented from undergoing deactivation of an acid catalyst used in the esterification reaction, can solve the problems such as clogging in apparatuses, and can ensure stable production of the (meth) acrylic esters for a long period of time, by using the purified (meth)acrylic acid obtained by the above process as the raw material.

PREFERRED EMBODIMENT FOR CARRYING OUT THE INVENTION

The present invention is described in detail below.

First, the process for purifying (meth)acrylic acid according to the present invention is explained. In the process for purifying (meth)acrylic acid according to the present invention, crude (meth)acrylic acid containing transition metal components as impurities is used as a raw material. As the method for producing such a crude (meth)acrylic acid, there may be used conventionally known methods. Namely, acrylic acid is produced by gas-phase oxidation of propane, propylene and/or acrolein, and methacrylic acid is produced by gas-phase oxidation of isobutylene and/or t-butyl alcohol. The process for producing the acrylic acid usually includes the following steps (1) to (5). Meanwhile, the following steps (1) to (5) are typical for the process for production of acrylic acid, but may also be applied to the production of methacrylic acid.

(1) Step of forming an acrylic acid-containing gas by an one-stage oxidation method in which acrylic acid is directly produced by reacting propane, propylene and/or acrolein (isobutylene and/or t-butyl alcohol in the case of methacrylic acid) with a molecular oxygen-containing gas in the presence of a molybdenum oxide-based solid oxidation catalyst, etc.; or a two-stage oxidation method in which propylene is first reacted with a molecular oxygen-containing gas in the presence of a molybdenum oxide-based solid oxidation catalyst, etc., in the first reaction zone to produce acrolein, and then the resultant acrolein is reacted with a molecular oxygen in the presence of the molybdenum oxide-based solid oxidation catalyst, etc., in the second reaction zone to produce acrylic acid.

(2) Step of bringing the thus obtained acrylic acid-containing gas into a counter-flow contact with water in an absorption column to produce an aqueous solution of crude acrylic acid.

(3) Step of extracting the resultant aqueous solution of crude acrylic acid with an organic solvent such as, for example, methyl isobutyl ketone and diisobutyl ketone, and then distilling the resultant extract to obtain an acrylic acid-containing liquid as a bottom fraction; or directly subjecting the resultant aqueous solution of crude acrylic acid together with an azeotropic agent such as toluene, butyl acetate and octane to azeotropic dehydration, for example, at a temperature of 80 to 100° C. under a pressure of 6.67 to 20 kPa to obtain an acrylic acid-containing liquid as a bottom fraction.

(4) Step of subjecting the thus obtained acrylic acid-containing liquid to distillation treatment to remove low-boiling components such as acetic acid therefrom, and then further subjecting the resultant bottom liquid to distillation treatment to obtain crude acrylic acid as a top fraction as well as high-boiling substances including an acrylic acid dimer as a bottom liquid.

(5) Step of further subjecting the acrylic acid dimer obtained as the bottom liquid to distillation treatment to obtain crude acrylic acid as a top fraction.

The crude acrylic acid obtained in the above steps (4) and (5) is further distilled by known methods to remove impurities such as maleic acids and aldehydes therefrom. As the distillation method, there may be used various methods such as simple distillation and precision distillation. The distillation treatment may be conducted by either a batch method or a continuous method. Of these methods, the continuous method is preferred from the industrial viewpoint. Also, as the distillation apparatus, there may be used conventionally known apparatuses. Meanwhile, in some cases, the crude acrylic acid may be directly subjected to the process for purification of (meth)acrylic acid according to the present invention without removing the impurities such as maleic acids and aldehydes therefrom.

Since the (meth)acrylic acid is an easily-polymerizable compound, the respective distillation steps described above are usually performed by adding a known polymerization inhibitor, i.e., a polymerization terminator or a polymerization retarder. Examples of the polymerization inhibitor may usually include copper compounds such as cupric chloride, copper acetate, copper carbonate, copper acrylate, copper dimethyldithiocarbamate, copper diethyldithiocarbamate and copper dibutyldithiocarbamate; and manganese compounds such as manganese dialkyldithiocarbamates (wherein the alkyl group is methyl, ethyl, propyl or butyl and may be the same or different from each other), manganese diphenyldithiocarbamate, manganese formate, manganese acetate, manganese octanoate, manganese naphthenate, manganese permanganate and manganese salts of ethylene-diaminetetraacetic acid. These polymerization inhibitors may be used in the form of a mixture of any two or more thereof, or may be used in combination with the other polymerization inhibitors.

Examples of the other polymerization inhibitors may include N-oxyl compounds such as tert-butyl nitroxide, 2,2,6,6-tetramethyl-4-hydroxypiperidyl-1-oxyl, 2,2,6,6-tetramethylpiperidyl-1-oxyl, 2,2,6,6-tetramethylpiperidino-oxyl, 4-hydroxy-2,2,6,6-tetramethylpiperidino-oxyl and 4,4',4"-tris-1-(2,2,6,6-tetramethylpiperidino-oxyl)phosphite; phenol compounds such as hydroquinone, methoquinone, pyrogallol, catechol and restrain; and phenothiazine compounds such as phenothiazine, bis-(α-methylbenzyl) phenothiazine, 3,7-dioctyl phenothiazine and bis-(α-dimethylbenzyl)phenothiazine. These other polymerization inhibitors may be used in the combination of any two or more thereof. The polymerization inhibitor is usually added in an amount of 1 to 1,000 ppm based on the crude (meth)acrylic acid.

The crude (meth)acrylic acid from which the impurities such as maleic acids and aldehydes are not removed, contains transition metal components in an amount of usually 1 to 10 ppm based on the crude (meth)acrylic acid. It is considered that the transition metal components are mixed in the crude (meth)acrylic acid owing to entrainment of splash of the above polymerization inhibitor used in the process for production of the (meth)acrylic acid upon the distillation step.

The transition metals mixed in the (meth)acrylic acid are metal elements belonging to Groups 7 to 12 of the 18-Group long-form Periodic Table. Specific examples of the transition metals may include manganese, iron, cobalt, nickel, copper and zinc. Of these transition metals, manganese tends to exert a significant influence on the esterification reaction catalyst used in the process for production of the (meth)acrylic esters. Therefore, it is preferable to remove manganese from the crude (meth)acrylic acid in the process for purifying (meth)acrylic acid according to the present invention.

In the process for purifying (meth)acrylic acid according to the present invention, water is added to the crude (meth)acrylic acid containing the above transition metals, and then the resultant mixture is contacted with an cation exchange resin. The amount of water added is usually 1 to 10% by weight, preferably 1 to 5% by weight based on the weight of the crude (meth)acrylic acid containing the transition metals. When the amount of water added is less than 1% by weight, the effect of enhancing a removability for removing the transition metal components from the crude (meth)acrylic acid may not be sufficiently exhibited. When the amount of water added is more than 10% by weight, the efficiency of the subsequent esterification reaction tends to be deteriorated in the case where the mixture of the crude (meth) acrylic acid and water is successively used in the process for production of (meth)acrylic esters.

Water may be added to the crude (meth)acrylic acid containing the transition metal components at any stage without particular limitations, as long as the stage is prior to contacting the crude (meth)acrylic acid with the cation exchange resin for removal of the transition metals. As the method of adding water to the crude (meth)acrylic acid containing the transition metal components, there may be used, for example, the method of directly connecting a conduit through which the crude (meth)acrylic acid is flowed, to a conduit for water, and the method of adding water to a reaction vessel provided to ensure intimate mixing and a sufficient residence time. Also, in the case of (meth) acrylic acid products, water may be directly added thereto.

In the present invention, the effect of water added to the crude (meth)acrylic acid is considered as follows, though it is not clearly known. That is, water added acts for expanding pores that are present around active sites for adsorption of the transition metal components in the cation exchange resin, and promoting adsorption of the transition metal components therein to, resulting in enhancement of removability for removing the transition metal components from the crude (meth)acrylic acid.

Next, the crude (meth)acrylic acid to which water is added, is contacted with the cation exchange resin to remove the transition metal components therefrom. As the cation exchange resin, there may be used various cation exchange resins without any particular limitations as to resin properties such as structure and cross-linking density thereof. For example, there may be preferably used porous-type or gel-type strong acid cation exchange resins. Of these resins, especially preferred are porous-type strong acid cation exchange resins. Examples of the porous-type strong acid cation exchange resins may include "MSC-1" produced by Dow Chemical Company, "PK-208", "PK-212", "PK-216", "PK-220" and "PK-228" all produced by Mitsubishi Chemical Corporation, "Amber List 16", "IR-116", "IR-118", "IR-122", "C-26", "C-26TR", "C-264" and "C-265" all produced by Rohm & Haas Co., Ltd., "SPC-108" and "SPC-112" both produced by Bayer AG, and "KC-470" produced by Sumitomo Chemical Co., Ltd. Examples of the gel-type strong acid cation exchange resins may include "HCR-S", "HCR-W2" and "HGR-W2" all produced by Dow Chemical Company, "SK-1B", "SK-106" and "SK-110" all produced by Mitsubishi Chemical Corporation, "Duolite C20H" and "Duolite C255LFH" both produced by Rohm & Haas Co., Ltd., and "K1221" and "K1431" both produced by Bayer AG. In addition, there may also be used weak acid cation exchange resins. These cation exchange resins may be used singly or in the form of a mixture of any two or more thereof.

The crude (meth)acrylic acid to which water is added may be contacted with the cation exchange resin, for example, by the method of flowing the crude (meth)acrylic acid through a fixed bed composed of the cation exchange resin. In this case, the amount of the crude (meth)acrylic acid flowed through the fixed bed is not particularly restricted, and usually 0.1 to 10 parts by volume per hour, preferably 1 to 5 parts by volume per hour based on one part by volume of the cation exchange resin. The temperature used upon contacting the crude (meth)acrylic acid with the cation exchange resin is preferably in the range of from room temperature to a boiling point of the (meth)acrylic acid from the standpoint of a good operating property. Further, the contacting procedure may be preferably performed under atmospheric pressure from the standpoint of a good operating property.

The (meth)acrylic acid treated by the purification process of the present invention contains the transition metal components in an amount of usually not more than 0.1 ppm, preferably not more than a detection limit based on the weight of the (meth)acrylic acid.

Next, the process for producing (meth)acrylic esters according to the second aspect of the present invention is explained below. In the process for producing (meth)acrylic esters according to the present invention, the purified (meth) acrylic acid obtained by the above process for purifying (meth)acrylic acid according to the present invention, and alcohol are subjected to esterification reaction in the presence of an acid catalyst.

Examples of the acid catalyst used in the esterification reaction may include inorganic acids such as sulfuric acid, organic acids such as p-toluenesulfonic acid and methanesulfonic acid, and solid acids such as cation exchange resins. In particular, in the case where the organic acid catalysts and the solid acid catalysts are used, the effect of using the purified (meth)acrylic acid from which the transition metal components are removed can be more remarkably exhibited.

Examples of the (meth)acrylic esters produced by the production process of the present invention may include methyl (meth)acrylate, ethyl (meth)acrylate, n-butyl (meth) acrylate, isobutyl (meth)acrylate, tert-butyl (meth)acrylate, 2-ethylhexyl (meth)acrylate, isononyl (meth)acrylate and methoxyethyl (meth)acrylate. Of these esters, preferred are those esters produced using alcohols having 4 or more carbon atoms. The esters produced using alcohols having 3 or less carbon atoms have a boiling point lower than that of water, so that it may be sometimes difficult to distil off water upon the esterification reaction.

The esterification reaction may be conducted by ordinary methods. That is, in the esterification reaction, the molar ratio between the (meth)acrylic acid and alcohol as raw materials, the kind and amount of catalyst used therein, the reaction methods and the reaction conditions may be appropriately determined according to the kind of alcohol used therein. The (meth)acrylic ester solution produced by the esterification reaction process may be further subjected to various known steps such as washing, liquid-liquid separation, extraction, evaporation and distillation for separation of the catalyst as well as concentration and purification of the reaction product, thereby obtaining the purified (meth) acrylic esters.

EXAMPLES

The present invention is described in more detail by Examples, but the Examples are only illustrative and not intended to limit the scope of the present invention. Meanwhile, the method for quantitative determination of manganese contained in acrylic acid which was used in the following Examples and Comparative Examples, is described below.

Quantitative Determination of Manganese:

As a pretreatment, a sample was thermally decomposed in the presence of a mixed acid of sulfuric acid and nitric acid, and then mixed with distilled water to prepare 50 mL of an aqueous solution. Next, the thus prepared aqueous solution was subjected to quantitative analysis by ICP-AES method using an ICP emission spectroscopic device "JY-138U" manufactured by Horiba Limited.

Example 1

An anhydrous manganese (II) acetate was added to a solution containing 99% by weight of acrylic acid and 1% by weight of distilled water such that the manganese concentration in the solution was 1,200 ppm by weight based on the weight of the solution, thereby preparing a manganese-containing acrylic acid solution. After maintaining the temperature of a fixed bed packed with 40 mL of a strong acid porous-type cation exchange resin "DIAION PK-216H" produced by Mitsubishi Chemical Corporation, at 25° C., the above-prepared manganese-containing acrylic acid solution was flowed through the fixed bed at a flow rate of one part by volume per hour based on one part by volume of the resin. After the elapse of 2 hours, 3 hours, 4 hours and 5 hours from initiation of flowing the solution through the fixed bed, respective effluents were recovered and subjected to analysis of manganese concentration therein. The manganese concentrations in the respective solutions before and after flowing the solution through the fixed bed are shown in Table 1.

TABLE 1

| Solution-flowing time | Manganese concentration in effluent (ppm by weight) |
| --- | --- |
| Before flowing | 1,200 |
| After 2 hours | Not detected |
| After 3 hours | Not detected |
| After 4 hours | 30 |
| After 5 hours | 100 |

Further, the thus obtained effluent and n-butanol as alcohol were subjected to continuous esterification reaction in the presence of p-toluenesulfonic acid as an organic acid catalyst using an ordinary esterification reaction apparatus. As a result, it was confirmed that no complex of the organic acid catalyst was precipitated even after the elapse of 120 hours, namely the continuous esterification reaction could be stably conducted.

Comparative Example 1

The same procedure as defined in Example 1 was conducted except that no distilled water was added. After the elapse of 2 hours, 3 hours and 4 hours from initiation of flowing the solution through the fixed bed, respective effluents were recovered and subjected to analysis of manganese concentration therein. The manganese concentrations in the recovered solutions before and after flowing the solution through the fixed bed are shown in Table 2.

TABLE 2

| Solution-flowing time | Manganese concentration in effluent (ppm by weight) |
| --- | --- |
| Before flowing | 1,200 |
| After 2 hours | 80 |
| After 3 hours | 480 |
| After 4 hours | 810 |

Further, the thus obtained effluent and n-butanol as alcohol were subjected to continuous esterification reaction in the presence of p-toluenesulfonic acid as an organic acid catalyst using an ordinary esterification reaction apparatus. As a result, it was confirmed that a nozzle of the apparatus was clogged by precipitates after the elapse of 40 hours. Therefore, the esterification reaction had to be terminated.

Example 2

The same procedure as defined in Example 1 was conducted except that distilled water was added in an amount of 5% by weight. After the elapse of 2 hours, 3 hours, 4 hours, 5 hours, 12 hours and 24 hours from initiation of flowing the solution through the fixed bed, respective effluents were recovered and subjected to analysis of manganese concentration therein. The manganese concentrations in the respective solutions before and after flowing the solution through the fixed bed are shown in Table 3.

TABLE 3

| Solution-flowing time | Manganese concentration in effluent (ppm by weight) |
| --- | --- |
| Before flowing | 1,200 |
| After 2 hours | Not detected |
| After 3 hours | Not detected |
| After 4 hours | Not detected |
| After 5 hours | Not detected |
| After 12 hours | Not detected |
| After 24 hours | 140 |

Example 3

The same procedure as defined in Example 2 was conducted except that the amount of acrylic acid flowed through the fixed bed was changed to 10 parts by volume per hour based on one part by volume of the resin. After the elapse of 0.5 hour and 2 hours from initiation of flowing the solution through the fixed bed, respective effluents were recovered and subjected to analysis of manganese concentration therein. The manganese concentrations in the respective solutions before and after flowing the solution through the fixed bed are shown in Table 4.

TABLE 4

| Solution-flowing time | Manganese concentration in effluent (ppm by weight) |
| --- | --- |
| Before flowing | 1,200 |
| After 0.5 hour | 10 |
| After 2 hours | 520 |

Comparative Example 2

The same procedure as defined in Example 3 was conducted except that no distilled water was added. After the elapse of 1 hour, 2.5 hours and 4 hours from initiation of flowing the solution through the fixed bed, respective effluents were recovered and subjected to analysis of manganese concentration therein. The manganese concentrations in the respective solutions before and after flowing the solution through the fixed bed are shown in Table 5.

TABLE 5

| Solution-flowing time | Manganese concentration in effluent (ppm by weight) |
|---|---|
| Before flowing | 1,200 |
| After 1 hour | 1,100 |
| After 2.5 hours | 1,100 |
| After 4 hours | 1,100 |

The invention claimed is:

1. A process for purifying (meth)acrylic acid by contacting crude (meth)acrylic acid containing transition metal components as impurities with a cation exchange resin to remove the transition metal component therefrom, water being previously added to the crude (meth)acrylic acid prior to contacting the crude (meth)acrylic acid with the cation exchange resin, wherein the transition metal component is manganese.

2. A process for producing a (meth)acrylic ester by reacting (meth)acrylic acid with alcohol in the presence of an acid catalyst, the (meth)acrylic acid obtained by the process as defined in claim 1 being used as the raw material.

3. A process according to claim 2, wherein the acid catalyst is a cation exchange resin or an organic acid.

4. A process according to claim 3, wherein the cation exchange resin is a porous type strong acid cation exchange resin.

* * * * *